United States Patent
Ibrahim et al.

(10) Patent No.: US 11,565,010 B2
(45) Date of Patent: Jan. 31, 2023

(54) SHOPPING CART SANITIZATION DEVICE

(71) Applicants: Nazih Ibrahim, Boca Raton, FL (US); Sami Ibrahim, Boca Raton, FL (US); Errin Gnadinger, Boca Raton, FL (US)

(72) Inventors: Nazih Ibrahim, Boca Raton, FL (US); Sami Ibrahim, Boca Raton, FL (US); Errin Gnadinger, Boca Raton, FL (US)

( * ) Notice: Subject to any disclaimer, the term of this patent is extended or adjusted under 35 U.S.C. 154(b) by 252 days.

(21) Appl. No.: 16/945,704

(22) Filed: Jul. 31, 2020

(65) Prior Publication Data

US 2022/0031875 A1 Feb. 3, 2022

(51) Int. Cl.
| A61L 2/10 | (2006.01) |
| B62B 3/14 | (2006.01) |
| A47F 10/04 | (2006.01) |
| A61L 2/26 | (2006.01) |

(52) U.S. Cl.
CPC ............... *A61L 2/10* (2013.01); *A47F 10/04* (2013.01); *A61L 2/26* (2013.01); *B62B 3/1404* (2013.01); *A61L 2202/11* (2013.01); *A61L 2202/121* (2013.01); *A61L 2202/14* (2013.01)

(58) Field of Classification Search
CPC .......... A61L 2/10; A61L 2/26; A61L 2202/11; A61L 2202/14; A61L 2202/121; A47F 10/04
See application file for complete search history.

(56) References Cited

U.S. PATENT DOCUMENTS

| 7,791,044 | B1 * | 9/2010 | Taylor | A61L 2/10 |
| | | | | 250/493.1 |
| 8,381,746 | B2 * | 2/2013 | Yoon | B08B 3/022 |
| | | | | 134/123 |
| 8,536,541 | B2 * | 9/2013 | Taylor | A61L 2/24 |
| | | | | 250/493.1 |
| 9,295,741 | B2 * | 3/2016 | Yerby | A61L 2/24 |
| 10,894,106 | B1 * | 1/2021 | Lopez | B60S 3/04 |
| 10,898,601 | B2 * | 1/2021 | Majdali | B60S 3/04 |
| 10,913,431 | B1 * | 2/2021 | Lopez | A61L 2/18 |
| 11,033,643 | B2 * | 6/2021 | Starkweather | A61L 2/10 |
| 11,090,399 | B2 * | 8/2021 | Starkweather | A61L 2/14 |
| 2005/0201910 | A1 * | 9/2005 | Shou | A61L 2/10 |
| | | | | 422/186 |

(Continued)

FOREIGN PATENT DOCUMENTS

KR    100893790 B1 *    4/2009    ............... A61L 2/10

*Primary Examiner* — Wyatt A Stoffa
(74) *Attorney, Agent, or Firm* — The Iwashko Law Firm, PLLC; Lev Ivan Gabriel Iwashko

(57) ABSTRACT

A shopping cart sanitization device, including a main body to receive at a first end at least one shopping cart therein, and a primary sanitization unit disposed within at least at least one portion of an interior of the main body, the primary sanitization unit including a sanitization body to automatically move from a second end of the main body to the first end of the main body in response to the main body receiving the at least one shopping cart, and at least one illumination unit disposed on at least at least one portion of the sanitization body to automatically illuminate UV light on the at least one shopping cart in response to the main body receiving the at least one shopping cart, such that the at least one illumination unit eliminates a pathogen.

10 Claims, 6 Drawing Sheets

(56) References Cited

U.S. PATENT DOCUMENTS

| | | | |
|---|---|---|---|
| 2006/0186358 A1* | 8/2006 | Couvillion | A61L 2/10 250/504 R |
| 2007/0012340 A1* | 1/2007 | Jones | A61L 2/10 134/131 |
| 2008/0178412 A1* | 7/2008 | Kiter | A61L 2/10 15/4 |
| 2012/0248332 A1* | 10/2012 | Kreitenberg | A63B 47/04 250/455.11 |
| 2014/0158910 A1* | 6/2014 | Fletcher | A61L 2/10 250/455.11 |
| 2017/0340760 A1* | 11/2017 | Starkweather | A61L 2/10 |
| 2021/0369015 A1* | 12/2021 | Nevitt | A61L 2/10 |
| 2022/0016279 A1* | 1/2022 | Johnson | A61L 2/10 |

* cited by examiner

SHOPPING CART SANITIZATION DEVICE

BACKGROUND

1. Field

The present general inventive concept relates generally to a sanitization device, and particularly, to a shopping cart sanitization device.

2. Description of the Related Art

A shopping cart is a wheeled cart that is usually provided by a store, such as a supermarket that allows a customer to store merchandise therein. The shopping cart improves a shopping experience of the customer by providing the customer a means to collect all the merchandise in a convenient location prior to purchasing the merchandise.

Unsurprisingly, the shopping cart is used by multiple customers throughout each day. As such, the shopping cart is touched by each customer, which can quickly lead to the spread of a pathogen, such as bacteria, viruses, fungi, and/or a parasite. For example, the recent pandemic involving the severe acute respiratory syndrome coronavirus 2 (SARS-CoV-2) is affecting many people worldwide. A known vector of transmission between humans of the SARS-CoV-2 is touching a contaminated surface and then touching a face.

Some methods of cleaning the shopping cart include spraying a handle with a disinfectant and/or wiping the handle of the shopping cart with a disinfectant wipe. However, these methods require active participation by the customer and/or an employee of the store to either spray and/or wipe the shopping cart. Also, other portions of the shopping cart are prone to be touched which can keep pathogens present.

Therefore, there is a need for a shopping cart sanitization device that can quickly disinfect a line of shopping carts.

SUMMARY

The present general inventive concept provides a shopping cart sanitization device.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a shopping cart sanitization device, including a main body to receive at a first end at least one shopping cart therein, and a primary sanitization unit disposed within at least at least one portion of an interior of the main body, the primary sanitization unit including a sanitization body to automatically move from a second end of the main body to the first end of the main body in response to the main body receiving the at least one shopping cart, and at least one illumination unit disposed on at least at least one portion of the sanitization body to automatically illuminate UV light on the at least one shopping cart in response to the main body receiving the at least one shopping cart, such that the at least one illumination unit eliminates a pathogen.

The main body may include a barrier disposed on at least a portion of the main body, and an inclined surface disposed within at least a portion of the main body to facilitate extraction of the at least one shopping cart from the main body.

The main body may receive the at least one shopping cart in response to the barrier being sufficiently closed.

The at least one illumination unit may illuminate in response to the barrier being sufficiently closed.

The at least one illumination unit may comprise at least at least one form of a UV light.

The main body may allow visible light with respect to humans to move therethrough and prevent the UV light from moving therethrough.

The main body may prevent the UV light from moving therethrough using polycarbonate or other transparent or translucent materials, either by merits of the other transparent or translucent materials or an addition of specialty coatings.

The main body may allow visible light with respect to humans to move therethrough and reflect or absorb the UV light toward the interior of the main body.

The main body may reflect or absorb the UV light using barium sulphate or any other reflective material.

The shopping cart sanitization device may further include a sensor disposed on at least a portion of the main body to detect receipt of the at least one shopping cart within the main body.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Figure 1A:
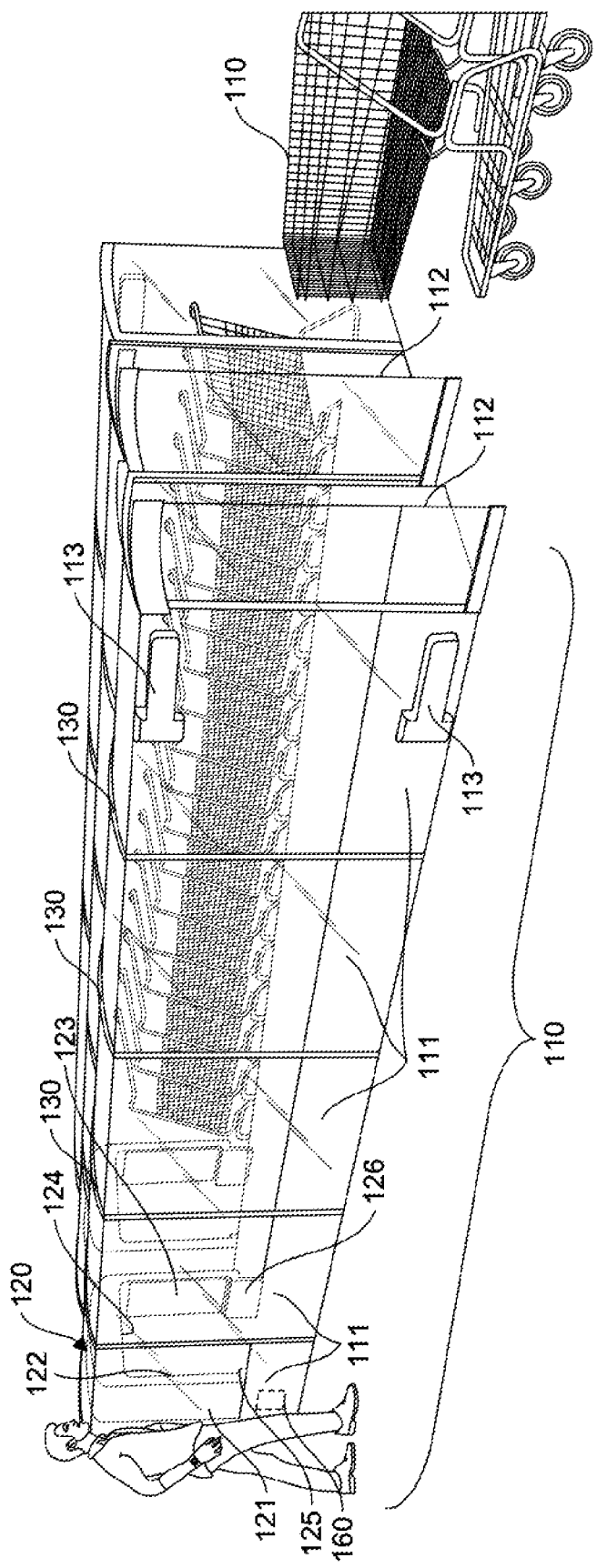
FIG. 1A illustrates an isometric view of a shopping cart sanitization device with a barrier in an opened and an extended position, according to an exemplary embodiment of the present general inventive concept.

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

LIST OF COMPONENTS

Shopping Cart Sanitization Device 100
Main Body 110
Body Sections 111
Barrier 112
Barrier-Clearing apparatuses 113
Inclined Surface 114
Inner Surface 115
Primary Sanitization Unit 120
Sanitization Body 121
First Illumination Unit 122
Second Illumination Unit 123
Third Illumination Unit 124
Fourth Illumination Unit 125
Fifth Illumination Unit 126
Support Frames 130
Rail Assembly 140
Rails 141
Cart Lock 142
Sensor 150
Power Source 160
Shopping Cart Sanitization Device 200
Main Body 210
Body Sections 211
Barrier 212
Barrier-Clearing Apparatus 213
Inclined Surface 214
Inner Surface 215
Primary Sanitization Unit 220
Sanitization Body 221
First Illumination Unit 222
Second Illumination Unit 223
Third Illumination Unit 224
Fourth Illumination Unit 225
Fifth Illumination Unit 226
Support Frames 230
Rail Assembly 240
Rails 241
Cart Lock 242
Sensor 250
Power Source 260

FIG. 1A illustrates an isometric view of a shopping cart sanitization device 100 with a barrier 112 in an opened and an extended position, according to an exemplary embodiment of the present general inventive concept.

Figure 1B:
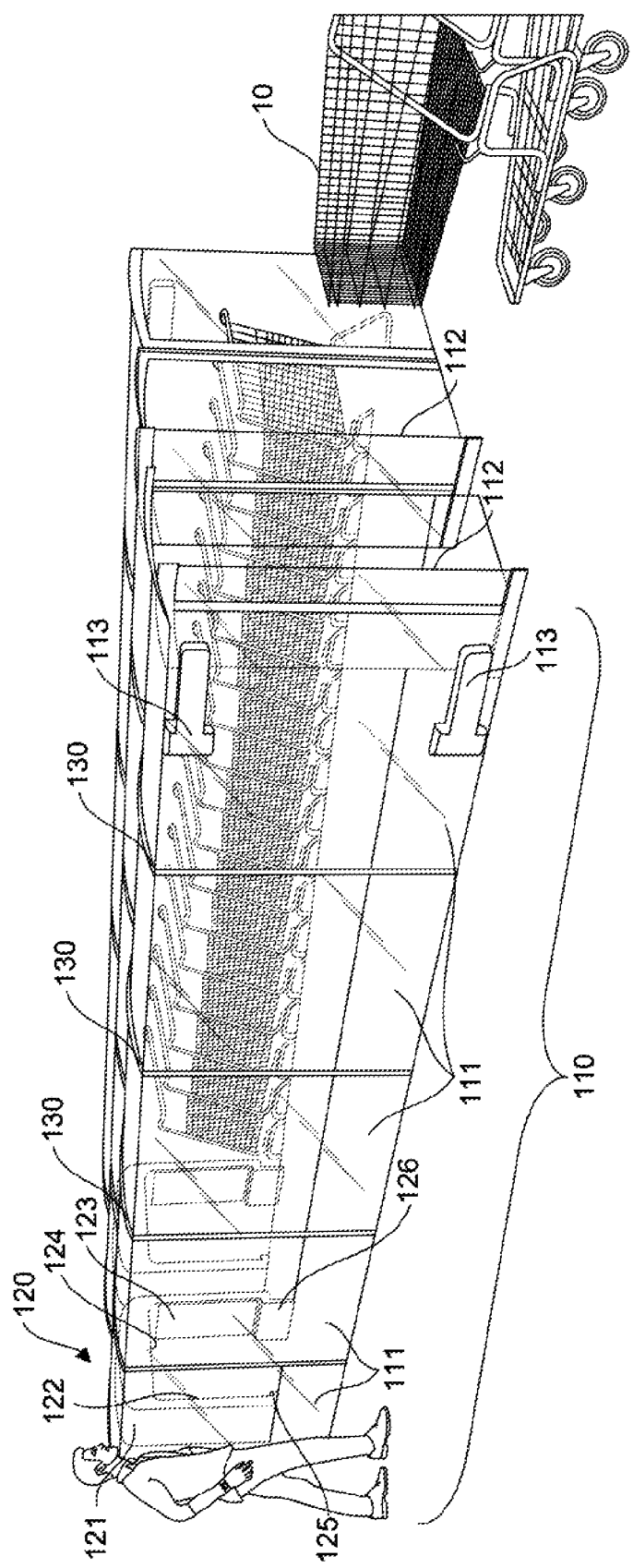
FIG. 1B illustrates an isometric view of the shopping cart sanitization device with the barrier in the opened and a retracted position, according to an exemplary embodiment of the present general inventive concept.

FIG. 1B illustrates an isometric view of the shopping cart sanitization device 100 with the barrier 112 in the opened and a retracted position, according to an exemplary embodiment of the present general inventive concept.

Figure 1C:
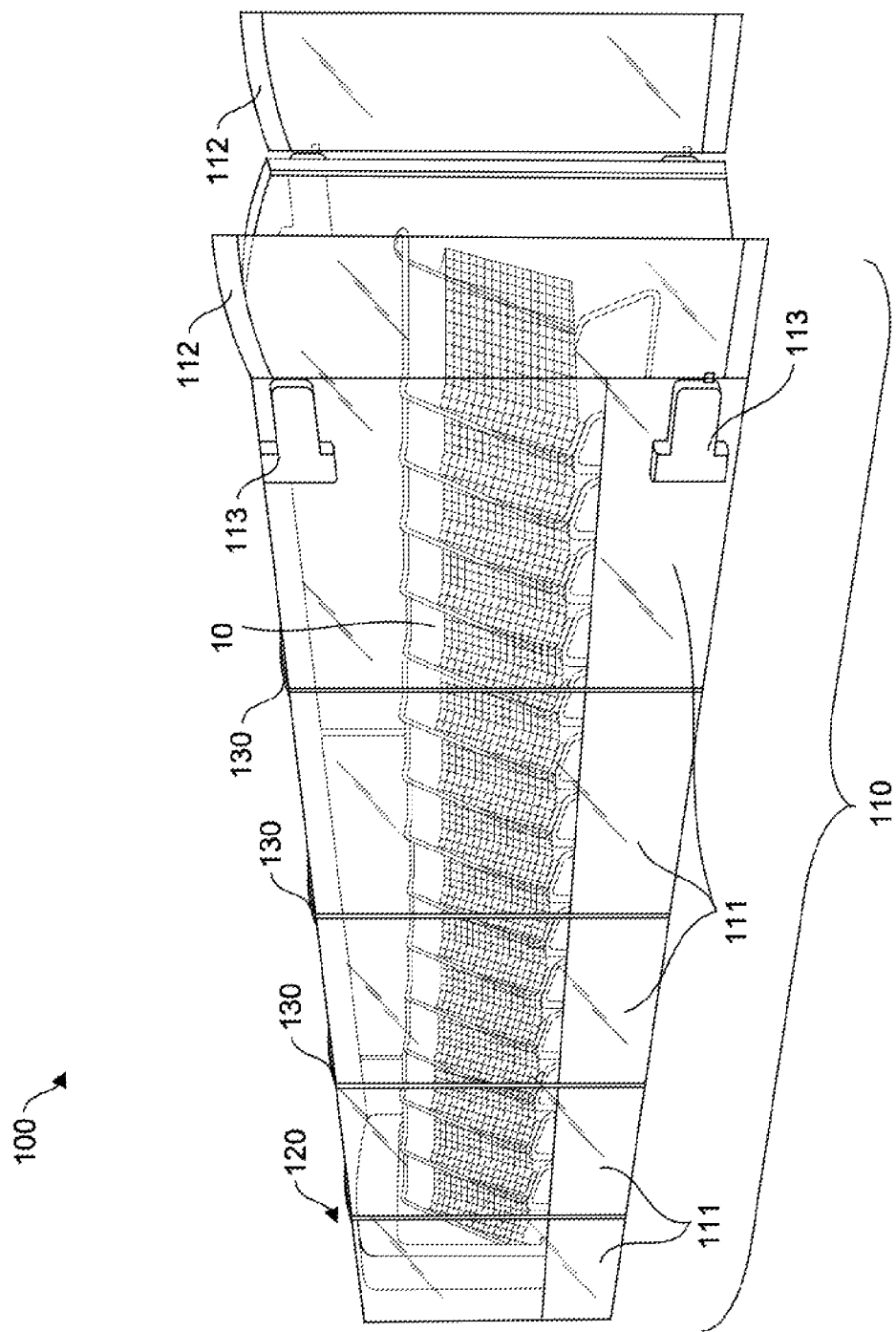
FIG. 1C illustrates an isometric view of the shopping cart sanitization device with a plurality of shopping carts stored therein, according to an exemplary embodiment of the present general inventive concept.

FIG. 1C illustrates an isometric view of the shopping cart sanitization device 100 with a plurality of shopping carts 10 stored therein, according to an exemplary embodiment of the present general inventive concept.

The shopping cart sanitization device 100 may be constructed from at least one of glass, metal, plastic, wood, and rubber, etc., but is not limited thereto and may be constructed from any material.

The shopping cart sanitization device 100 may include a main body 110, a primary sanitization unit 120, a plurality of support frames 130, a rail assembly 140, a sensor 150, and a power source 160, but is not limited thereto.

Referring to FIGS. 1A through 1C, the main body 110 may be constructed of an ultraviolet (UV) light filtered glass, such as polycarbonate or other transparent or translucent materials, either by merits of the other transparent or translucent materials or an addition of specialty coatings. In particular, the main body 110 may allow visible light with respect to humans to move therethrough, but prevent UV light from moving (i.e. transmission) therethrough. For example, UV light is electromagnetic radiation having a wavelength range of between 400 nanonmeters (nm) and 100 nm. Furthermore, the UV light may include many different forms, including, but not limited to, UVA, UVB, UVC, near ultraviolet, middle ultraviolet, far ultraviolet, vacuum ultraviolet, and any other form of ultraviolet light. Also, instead of UV filtered glass, the main body 110 may have a UV coating and/or tinting that prevents UV light from moving therethrough, such as organic dyes and/or metallic oxide pigments. The main body 110 may be constructed to be highly durable and shatterproof.

Please note that throughout this detailed description, the term "transparent" may also mean "semi-transparent," such that an object may be seen at least partially therethrough.

Referring again to FIGS. 1A through 1C, the main body 110 is illustrated to have a rectangular prism shape. However, the main body 110 may be rectangular, circular, conical, triangular, pentagonal, hexagonal, heptagonal, octagonal, or any other shape known to one of ordinary skill in the art, but is not limited thereto.

Alternatively, the main body 110 may use a UV reflective coating, such that the UV light within the main body 110 may reflect toward an interior of the main body 110. For example, the UV reflective coating may include barium sulphate or any other reflective material.

The main body 110 may include a plurality of body sections 111, a barrier 112, a plurality of barrier-clearing apparatuses 113, an inclined surface 114, and an inner surface 115, but is not limited thereto.

Each of the plurality of body sections 111 may have a length and/or a width equivalent to each other. In other words, each of the plurality of body sections 111 may be equivalent in size. However, the plurality of body sections 111 may differ in length and/or width based on a preference of a user and/or a manufacturer.

Each of the plurality of body sections 111 may be removably connected to each other, such that the main body 110 may vary in length. As such, the main body 110 is formed from the plurality of body sections 111.

Referring again to FIGS. 1A through 1O, the barrier 112 may be disposed on at least at least one portion of a first end of the main body 110. The barrier 112 may include two barriers or a single barrier. The barrier 112 may be constructed of the UV light filtered glass, similar to the main body 110. In other words, the barrier 112 may prevent the UV light from moving therethrough and/or reflecting the UV light toward the interior of the main body 112.

The barrier 112 may open allow at least one shopping cart 10 to be received through an entrance into the main body 110, such that the main body 110 may store the at least one shopping cart 10 therein.

Although the present general concept is directed to a shopping cart sanitization device 100 that allows at least one shopping cart 10 to be stored therein, the present general inventive concept is not limited thereto. In other words, the shopping cart 10 may be a shopping cart, a wheelchair, a gurney, a motorized device, a scooter, or any other type of object that may require sanitization. This applied to all embodiments of the present general inventive concept.

The plurality of barrier-clearing apparatuses 113 may be disposed on at least at least one portion of the main body 110, such that a first set of the plurality of re 113 is disposed on a first side of the main body 110 and a second set of the plurality of barrier-clearing apparatuses 113 disposed on a second side of the main body 110. The plurality of barrier-clearing apparatuses 113 may be removably connected to the barrier 112. Moreover, the barrier 112 may move in a first lateral direction or a second lateral direction within the barrier-clearing apparatuses 113 from extended in a first position to at least partially retracted in a second position while the barrier 112 is opened. As such, the barrier-clearing apparatuses 113 may receive the barrier 112 along an outer surface of the main body 110. Therefore, the barrier-clearing apparatuses 113 may prevent damage to the barrier 112 while the barrier 112 is disposed on the first side and the second side the main body 110.

Conversely, the barrier 112 may move in the second lateral direction or the first lateral direction within the barrier-clearing apparatuses 113 from retracted in the second position to extended in the first position, such that the barrier 112 may be closed.

The inclined surface 114 may be disposed within at least at least one portion of the main body 110. The inclined surface 114 may facilitate entry of the at least one shopping cart 10 therein. Alternatively, the inclined surface 114 may facilitate extraction of the at least one shopping cart 10 from within the main body 110, such that the inclined surface 114 may allow the at least one shopping cart 10 to roll down thereupon.

The inner surface 115 may be disposed within the interior of the main body 110. The inner surface 115 may receive the at least one shopping cart 10 thereupon. Additionally, the inner surface 115 may be a conveyor belt to move the at least one shopping cart 10 into the interior of the main body 110 and/or an exterior (i.e. outside) of the main body 110.

Figure 2:
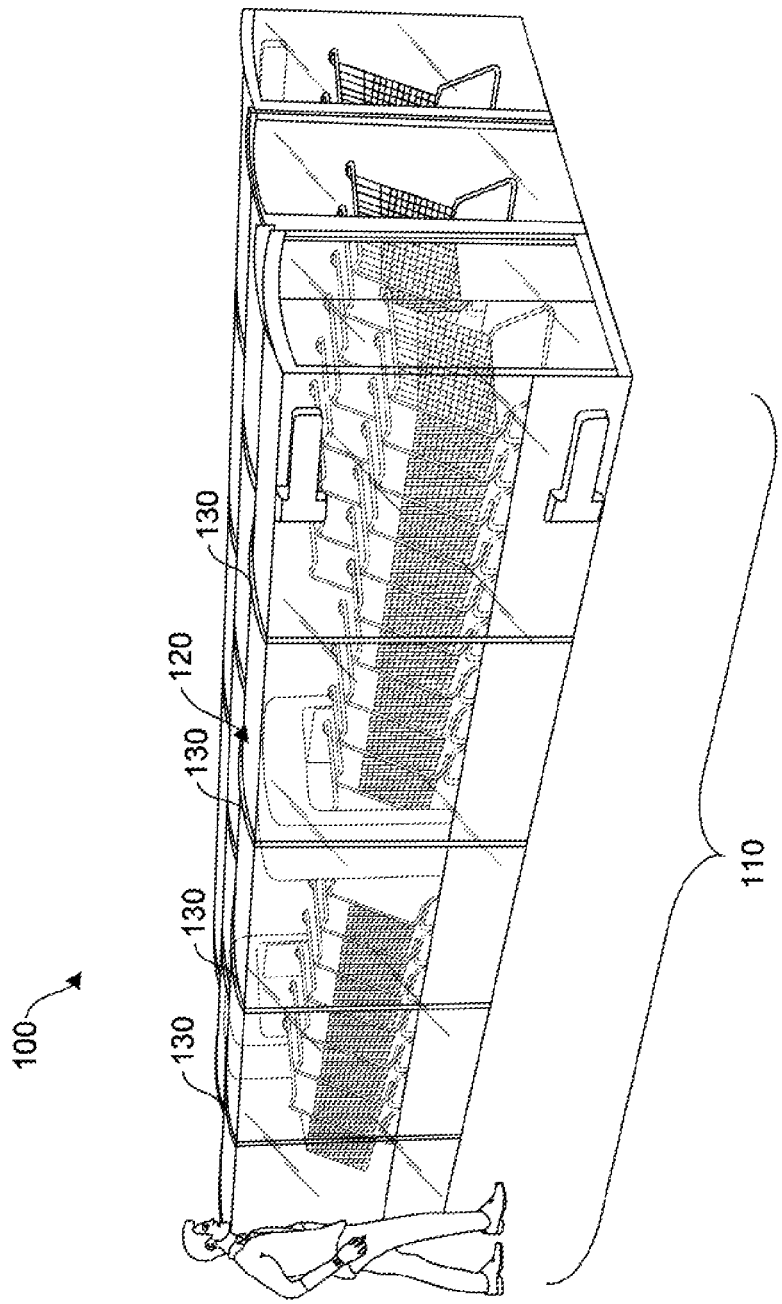
FIG. 2 illustrates an isometric view of the shopping cart sanitization device with a primary sanitization unit moving within a main body, according to an exemplary embodiment of the present general inventive concept.

FIG. 2 illustrates an isometric view of the shopping cart sanitization device 100 with a primary sanitization unit 120 moving within a main body 110, according to an exemplary embodiment of the present general inventive concept.

The primary sanitization unit 120 may include a sanitization body 121, a first illumination unit 122, a second illumination unit 123, a third illumination unit 124, a fourth illumination unit 125, and a fifth illumination unit 126, but is not limited thereto.

The primary sanitization unit 120 may be disposed within at least at least one portion of the interior of the main body 110.

Referring to FIGS. 1A through 2, the sanitization body 121 is illustrated to have a U-shape. However, the sanitization body 121 may be rectangular, circular, conical, triangular, pentagonal, hexagonal, heptagonal, octagonal, or any other shape known to one of ordinary skill in the art, but is not limited thereto.

The first illumination unit 122, the second illumination unit 123, the third illumination unit 124, the fourth illumination unit 125, and the fifth illumination unit 126 may include a UV light, but is not limited thereto. More specifically, the UV light used may be a UVC light, such that the UV light is a germicidal to illuminate, irradiate, and/or eliminate a pathogen.

The first illumination unit 122 may be disposed on at least at least one portion of a top portion of a first arm of the sanitization body 121. The second illumination unit 123 may be disposed on at least at least one portion of a top portion of a second arm of the sanitization body 121. The third illumination unit 124 may be disposed on at least at least one portion of a top of the sanitization body 121, such that the third illumination unit 124 is oriented toward a ground surface (i.e. down). The fourth illumination unit 125 may be disposed on at least at least one portion of a bottom portion of the first arm of the sanitization body 121. The fifth illumination unit 126 may be disposed on at least at least one portion of a bottom portion of the second arm of the sanitization body 121.

The first illumination unit 122, the second illumination unit 123, the third illumination unit 124, the fourth illumination unit 125, and/or the fifth illumination unit 126 may illuminate in response to closure of the barrier 112. In other words, the first illumination unit 122, the second illumination unit 123, the third illumination unit 124, the fourth illumination unit 125, and/or the fifth illumination unit 126 may illuminate automatically after the barrier 112 is closed.

Additionally, the sanitization body 121 may move in the first lateral direction or the second lateral direction from a second end of the main body 110 toward the first end of the main body 110 in response to closure of the barrier 112. In other words, the sanitization body 121 may move automatically after the barrier 112 is closed. Subsequently, the sanitization body 121 may move in the second lateral direction or the first lateral direction from the first end of the main body 110 toward the second end after reaching the first end of the main body. As such, the sanitization body 121 may move over the at least one shopping cart 10 at least twice. However, the sanitization body 121 may move over the at least one shopping cart 10a predetermined number of times based on the preference of the user and/or the manufacturer.

Therefore, the sanitization body 121, the first illumination unit 122, the second illumination unit 123, the third illumination unit 124, the fourth illumination unit 125, and/or the fifth illumination unit 126 may sanitize the at least one shopping cart 10 in response to illuminating the UV light thereupon. Moreover, the sanitization body 121, the first illumination unit 122, the second illumination unit 123, the third illumination unit 124, the fourth illumination unit 125, and/or the fifth illumination unit 126 may illuminate an entirety of the at least one shopping cart 10 due to movement of the sanitization body 121.

Furthermore, the sanitization body 121 may stop moving in response to opening the barrier 112. Also, the first illumination unit 122, the second illumination unit 123, the third illumination unit 124, the fourth illumination unit 125, and/or the fifth illumination unit 126 may stop illuminating in response to opening the barrier 112. As such, the UVC light emitted from the first illumination unit 122, the second illumination unit 123, the third illumination unit 124, the fourth illumination unit 125, and/or the fifth illumination unit 126 may be prevented from causing injury to a living organism outside the main body 110.

Each of the plurality of support frames 130 may include a rod, a bar, and a, but is not limited thereto.

The plurality of support frames 130 may be removably disposed on at least at least one portion of each connection between each of the plurality of body sections 111. As such, the plurality of support frames 130 may connect each of the plurality body sections 111 to each other.

Figure 3:
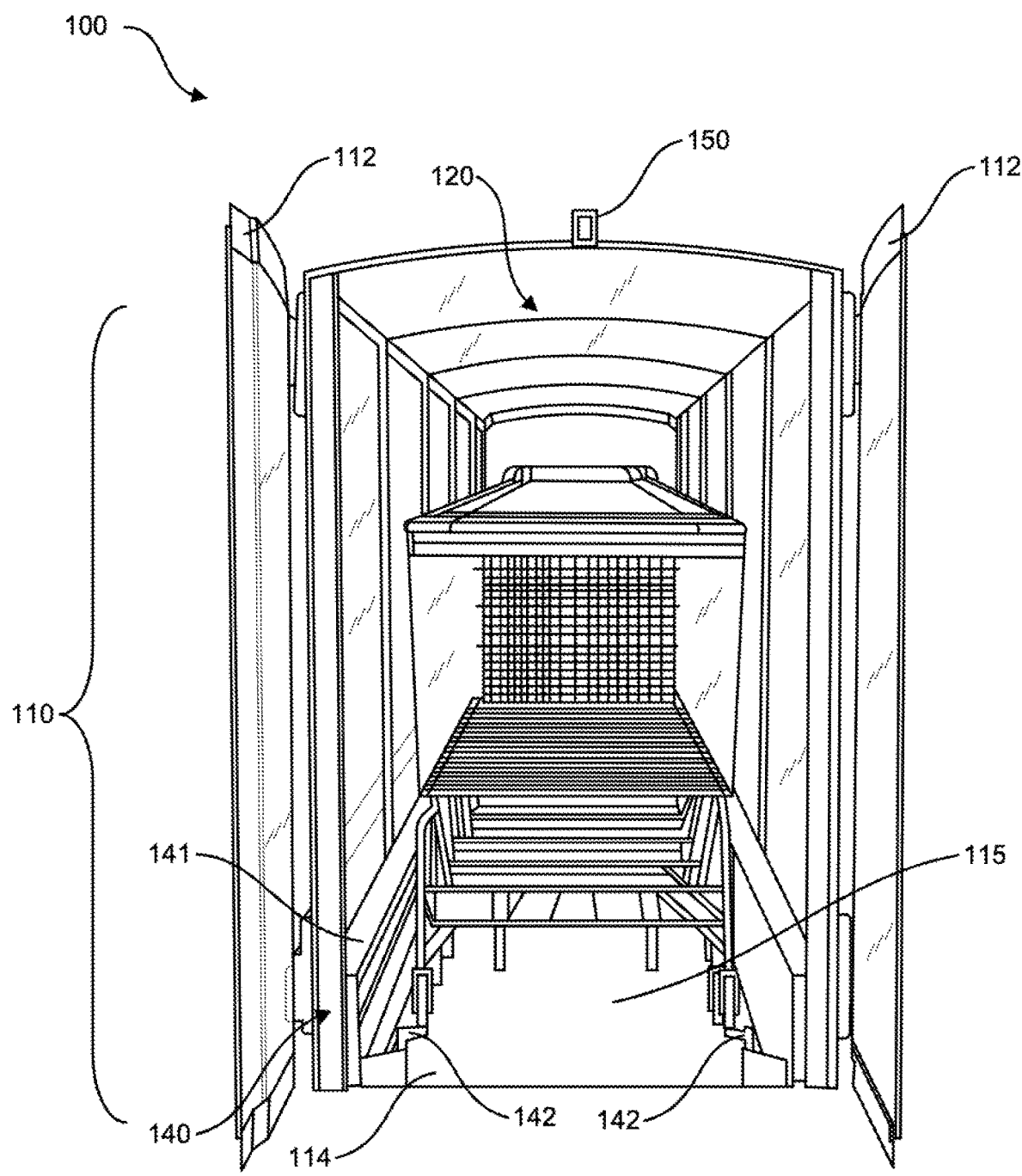
FIG. 3 illustrates a rear view of the shopping cart sanitization device, according to an exemplary embodiment of the present general inventive concept.

FIG. 3 illustrates a rear view of the shopping cart sanitization device 100, according to an exemplary embodiment of the present general inventive concept.

The rail assembly 140 may include a plurality of rails 141 and a cart lock 142, but is not limited thereto.

The plurality of rails 141 may be disposed on at least at least one portion of a base within the main body 110. The plurality of rails 141 may receive and connect to the at least one shopping cart 10 therein. Moreover, the plurality of rails 141 may prevent the at least one shopping cart 10 from lateral movement within the main body 110, such that the at least one shopping cart 10 may move in a straight line within the main body 110.

Furthermore, the plurality of rails 141 may move the at least one shopping cart 10 therein in response to the at least one shopping cart 10 contacting the plurality of rails 141. In other words, the plurality of rails 141 may automatically move the at least one shopping cart 10 from the first end of the main body 110 to at least partially toward the second end of the main body 110 in response to a number of shopping carts already within the main body 110 and/or being moved into the main body 110.

Also, the sanitization body 121 may be connected to a top surface of the plurality of rails 141. Moreover, the sanitization body 121 may move on the plurality of rails 141.

The cart lock 142 may be disposed within at least at least one portion of the rails 141. The cart lock 142 may prevent at least one shopping cart 10 from moving out of the plurality of rails 141. However, the cart lock 142 may release the at least one shopping cart 10 in response to receive a predetermined amount of force thereto. In other words, the cart lock 142 may release the at least one shopping cart 10 in response to retrieval by the user, but would not release the at least one shopping cart 10 while remaining within the plurality of rails 141.

The sensor 150 may be disposed on at least at least one portion of the main body 110. The sensor 150 may detect approach of the at least one shopping cart 10 toward the barrier 112 and/or the main body 110. Subsequently, the barrier 112 may open in response to detection of the at least one shopping cart 10 by the sensor 150, or alternatively, detection of a presence of human or non-human beings, which would also preclude the UV system. Moreover, the primary sanitization unit 120, the plurality of support frames 130, and/or the rail assembly 140 may activate in response to detection of the at least one shopping cart 10 being received within the main body 110 and/or closure of the barrier 112. Also, the barrier 112 may close in response to detection of the at least one shopping cart 10 moved within the main body 110.

After the primary sanitization unit 120 has completed sanitization, the barrier 112 may open in response to detection of completion by the sensor 150.

Alternatively, the sensor 150 may be replaced with a button and/or a control panel, such that manual input from the user controls operation of the barrier 112, the primary sanitization unit 120, and/or the rail assembly 140.

The power source 160 may include a battery, a solar cell, and a power inlet, but is not limited thereto.

The power source may provide power to the primary sanitization unit 120, the rail assembly 140, and/or the sensor 150.

Therefore, the shopping cart sanitization device 100 may disinfect a plurality of shopping carts 10 due to the numerous UV illumination units. Also, the shopping cart sanitization device 100 may eliminate all pathogens from the at least one shopping cart 10 due to movement of the primary sanitization unit 120.

Figure 4:
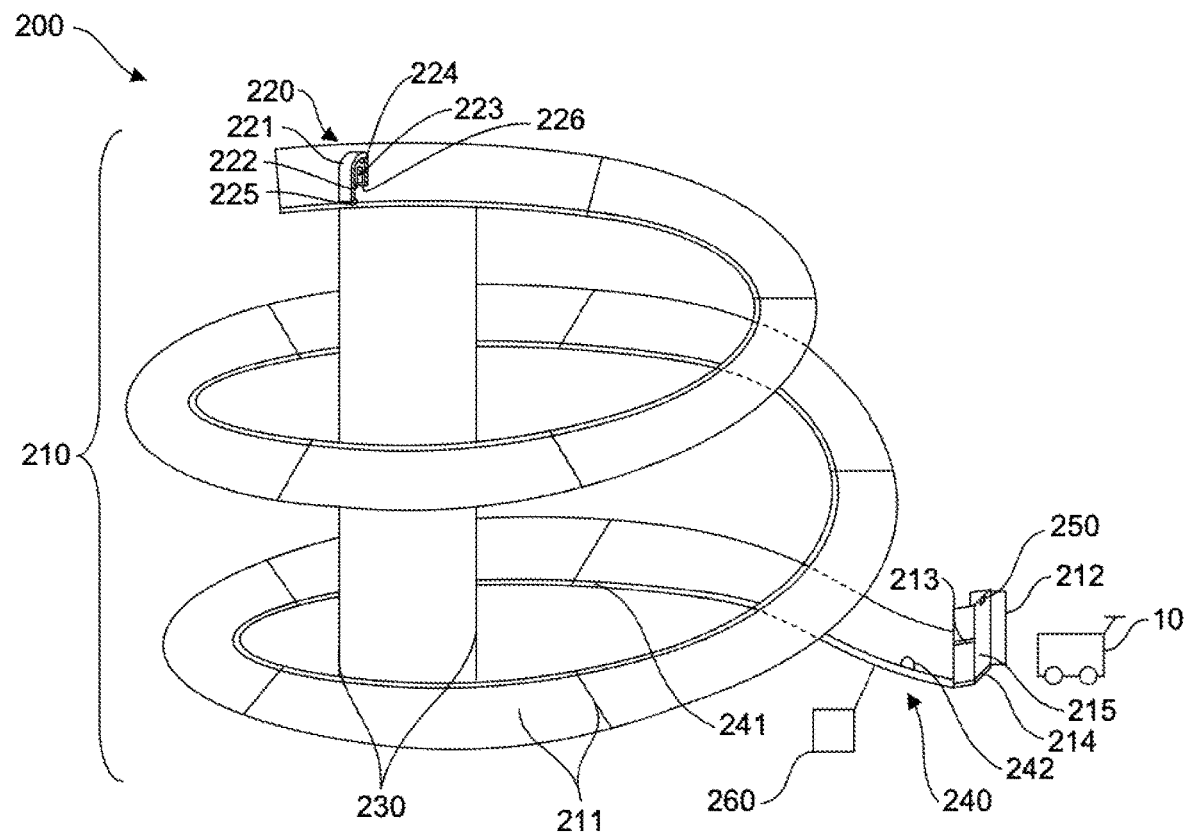
FIG. 4 illustrates a side perspective view of a shopping cart sanitization device, according to another exemplary embodiment of the present general inventive concept.

FIG. 4 illustrates a side perspective view of a shopping cart sanitization device 200, according to another exemplary embodiment of the present general inventive concept.

The shopping cart sanitization device 200 may be constructed from at least one of glass, metal, plastic, wood, and rubber, etc., but is not limited thereto and may be constructed from any material.

The shopping cart sanitization device 200 may include a main body 210, a primary sanitization unit 220, a plurality of support frames 230, a rail assembly 240, a sensor 250, and a power source 260, but is not limited thereto.

Referring to FIG. 4, the main body 210 may be constructed of an ultraviolet (UV) light filtered glass, such as polycarbonate or other transparent or translucent materials, either by merits of the other transparent or translucent materials or an addition of specialty coatings. In particular, the main body 210 may allow visible light with respect to humans to move therethrough, but prevent UV light from moving (i.e. transmission) therethrough. For example, UV light is electromagnetic radiation having a wavelength range of between 400 nanometers (nm) and 100 nm. Furthermore, the UV light may include UVA, UVB, UVC, near ultraviolet, middle ultraviolet, far ultraviolet, vacuum ultraviolet, and any other form of ultraviolet light. Also, instead of UV filtered glass, the main body 210 may have a UV coating and/or tinting that prevents UV light from moving therethrough, such as organic dyes and/or metallic oxide pigments. The main body 210 may be constructed to be highly durable and shatterproof.

Referring again to FIG. 4, the main body 210 is illustrated to have a spiral shape. However, the main body 210 may be rectangular, circular, conical, triangular, pentagonal, hexagonal, heptagonal, octagonal, or any other shape known to one of ordinary skill in the art, but is not limited thereto.

Alternatively, the main body 210 may use a UV reflective coating, such that the UV light within the main body 210 may reflect toward an interior of the main body 210. For example, the UV reflective coating may include barium sulphate or any other reflective material.

The main body 210 may include a plurality of body sections 211, a barrier 212, a plurality of barrier-clearing apparatuses 213, an inclined surface 214, and an inner surface 215, but is not limited thereto.

Each of the plurality of body sections 211 may have a length and/or a width equivalent to each other. In other words, each of the plurality of body sections 211 may be equivalent in size. However, the plurality of body sections 211 may differ in length and/or width based on a preference of a user and/or a manufacturer.

Each of the plurality of body sections 211 may be removably connected to each other, such that the main body 210 may vary in length. As such, the main body 210 is formed from the plurality of body sections 211.

Referring again to FIG. 4, the barrier 212 may be disposed on at least at least one portion of a first end of the main body 210. The barrier 212 may include two barriers or a single barrier. The barrier 212 may be constructed of the UV light filtered glass, similar to the main body 210. In other words, the barrier 212 may prevent the UV light from moving therethrough and/or reflecting the UV light toward the interior of the main body 212.

The barrier 212 may open allow at least one shopping cart 10 to be received through an entrance into the main body 210, such that the main body 210 may store the at least one shopping cart 10 therein.

The plurality of barrier-clearing apparatuses 213 may be disposed on at least at least one portion of the first end of the main body 210, such that a first set of the plurality of barrier-clearing apparatuses 213 is disposed on a first side of the main body 210 and a second set of the plurality of barrier-clearing apparatuses 213 disposed on a second side of the main body 210. The plurality of barrier-clearing apparatuses 213 may be removably connected to the barrier 212. Moreover, the barrier 212 may move in a first lateral direction or a second lateral direction within the barrier-clearing apparatuses 213 from extended in a first position to at least partially retracted in a second position while the barrier 212 is opened. As such, the barrier-clearing apparatuses 213 may receive the barrier 212 along an outer surface of the main body 210. Therefore, the barrier-clearing apparatuses 213 may prevent damage to the barrier 212 while the barrier 212 is disposed on the first side and the second side the main body 210.

Conversely, the barrier 212 may move in the second lateral direction or the first lateral direction within the barrier-clearing apparatuses 213 from retracted in the second position to extended in the first position, such that the barrier 212 may be closed.

The inclined surface 214 may be disposed within at least at least one portion of the main body 210. The inclined surface 214 may facilitate entry of the at least one shopping cart 10 therein. Alternatively, the inclined surface 214 may facilitate extraction of the at least one shopping cart 10 from within the main body 210, such that the inclined surface 214 may allow the at least one shopping cart 10 to roll down thereupon.

The inner surface 215 may be disposed within the interior of the main body 210. The inner surface 215 may receive the at least one shopping cart 10 thereupon. Additionally, the inner surface 215 may be a conveyor belt to move the at least one shopping cart 10 into the interior of the main body 210 and/or an exterior (i.e. outside) of the main body 210.

The primary sanitization unit 220 may include a sanitization body 221, a first illumination unit 222, a second illumination unit 223, a third illumination unit 224, a fourth illumination unit 225, and a fifth illumination unit 226, but is not limited thereto.

The primary sanitization unit 220 may be disposed within at least at least one portion of the interior of the main body 210.

Referring again to FIG. 4, the sanitization body 221 is illustrated to have a U-shape. However, the sanitization body 221 may be rectangular, circular, conical, triangular, pentagonal, hexagonal, heptagonal, octagonal, or any other shape known to one of ordinary skill in the art, but is not limited thereto.

The first illumination unit 222, the second illumination unit 223, the third illumination unit 224, the fourth illumination unit 225, and the fifth illumination unit 226 may include a UV light, but is not limited thereto. More specifically, the UV light used may be a UVC light, such that the UV light is a germicidal to illuminate, irradiate, and/or eliminate a pathogen.

The first illumination unit 222 may be disposed on at least at least one portion of a top portion of a first arm of the sanitization body 221. The second illumination unit 223 may be disposed on at least at least one portion of a top portion of a second arm of the sanitization body 221. The third illumination unit 224 may be disposed on at least at least one portion of a top of the sanitization body 221, such that the third illumination unit 224 is oriented toward a ground surface (i.e. down). The fourth illumination unit 225 may be disposed on at least at least one portion of a bottom portion of the first arm of the sanitization body 221. The fifth illumination unit 226 may be disposed on at least at least one portion of a bottom portion of the second arm of the sanitization body 221.

The first illumination unit 222, the second illumination unit 223, the third illumination unit 224, the fourth illumination unit 225, and/or the fifth illumination unit 226 may illuminate in response to closure of the barrier 212. In other words, the first illumination unit 222, the second illumination unit 223, the third illumination unit 224, the fourth illumination unit 225, and/or the fifth illumination unit 226 may illuminate automatically after the barrier 212 is closed.

Additionally, the sanitization body 221 may move in the first lateral direction or the second lateral direction from a second end of the main body 210 toward the first end of the main body 210 in response to closure of the barrier 212. In other words, the sanitization body 221 may move automatically after the barrier 212 is closed. Subsequently, the sanitization body 221 may move in the second lateral direction or the first lateral direction from the first end of the main body 210 toward the second end after reaching the first end of the main body. As such, the sanitization body 221 may move over the at least one shopping cart 10 at least twice. However, the sanitization body 221 may move over the at least one shopping cart 10a predetermined number of times based on the preference of the user and/or the manufacturer.

Therefore, the sanitization body 221, the first illumination unit 222, the second illumination unit 223, the third illumination unit 224, the fourth illumination unit 225, and/or the fifth illumination unit 226 may sanitize the at least one shopping cart 10 in response to illuminating the UV light thereupon. Moreover, the sanitization body 221, the first illumination unit 222, the second illumination unit 223, the third illumination unit 224, the fourth illumination unit 225, and/or the fifth illumination unit 226 may illuminate an entirety of the at least one shopping cart 10 due to movement of the sanitization body 221.

Referring again to FIG. 4, the second end of the main body 210 is illustrated to be at a higher vertical position with respect to the first end of the main body 210. In other words, the second end of the main body 210 may elevate the at least one shopping cart 10 to the higher vertical position than another at least one shopping cart 10 disposed at the first end of the main body 210. Moreover, the primary sanitization device 210 may move in the first lateral direction or the second lateral direction from the second end of the main body 210 toward the first end of the main body 210 in a circular downward direction. Conversely, the primary sanitization device 210 may move in the second lateral direction or the first lateral direction from the first end of the main body 210 toward the second end of the main body 210 in a circular upward direction.

Furthermore, the sanitization body 221 may stop moving in response to opening the barrier 212. Also, the first illumination unit 222, the second illumination unit 223, the third illumination unit 224, the fourth illumination unit 225, and/or the fifth illumination unit 226 may stop illuminating in response to opening the barrier 212. As such, the UVC light emitted from the first illumination unit 222, the second illumination unit 223, the third illumination unit 224, the fourth illumination unit 225, and/or the fifth illumination unit 226 may be prevented from causing injury to a living organism outside the main body 210.

Each of the plurality of support frames 230 may include a rod, a bar, and a tube, but is not limited thereto.

The plurality of support frames 230 may be removably disposed on at least at least one portion of the main body 210. Additionally, the plurality of support frames 230 may support each of the plurality of body sections 211 of the main body 210 thereupon.

The rail assembly 240 may include a plurality of rails 241 and a cart lock 242, but is not limited thereto.

The plurality of rails 241 may be disposed on at least at least one portion of a base within the main body 210. The plurality of rails 241 may receive and connect to the at least one shopping cart 10 therein. Moreover, the plurality of rails 241 may prevent the at least one shopping cart 10 from lateral movement within the main body 210, such that the at least one shopping cart 10 may move in a straight line within the main body 210.

Furthermore, the plurality of rails 241 may move the at least one shopping cart 10 therein in response to the at least one shopping cart 10 contacting the plurality of rails 241. In other words, the plurality of rails 241 may automatically move the at least one shopping cart 10 from the first end of the main body 210 to at least partially toward the second end of the main body 210 in response to a number of shopping carts already within the main body 210 and/or being moved into the main body 210.

Also, the sanitization body 221 may be connected to a top surface of the plurality of rails 241. Moreover, the sanitization body 221 may move on the plurality of rails 241.

The cart lock 242 may be disposed within at least at least one portion of the rails 241. The cart lock 242 may prevent at least one shopping cart 10 from moving out of the plurality of rails 241. However, the cart lock 242 may release the at least one shopping cart 10 in response to receive a predetermined amount of force thereto. In other words, the cart lock 242 may release the at least one shopping cart 10 in response to retrieval by the user, but would not release the at least one shopping cart 10 while remaining within the plurality of rails 241.

The sensor 250 may be disposed on at least at least one portion of the main body 210. The sensor 250 may detect approach of the at least one shopping cart 10 toward the barrier 212 and/or the main body 210. Subsequently, the barrier 212 may open in response to detection of the at least one shopping cart 10 by the sensor 250. Moreover, the primary sanitization unit 220, the plurality of support frames 230, and/or the rail assembly 240 may activate in response to detection of the at least one shopping cart 10 being received within the main body 210 and/or closure of the barrier 212. Also, the barrier 212 may close in response to detection of the at least one shopping cart 10 moved within the main body 210.

After the primary sanitization unit 220 has completed sanitization, the barrier 212 may open in response to detection of completion by the sensor 250.

Alternatively, the sensor 250 may be replaced with a button and/or a control panel, such that manual input from the user controls operation of the barrier 212, the primary sanitization unit 220, and/or the rail assembly 240.

The power source 260 may include a battery, a solar cell, and a power inlet, but is not limited thereto.

The power source may provide power to the primary sanitization unit 220, the rail assembly 240, and/or the sensor 250.

Therefore, the shopping cart sanitization device 200 may disinfect a plurality of shopping carts 10 due to the numerous UV illumination units. Also, the shopping cart sanitization device 200 may eliminate all pathogens from the at least one shopping cart 10 due to movement of the primary sanitization unit 220.

The present general inventive concept may include a shopping cart sanitization device 100, including a main body 110 to receive at a first end at least one shopping cart 10 therein, and a primary sanitization unit 120 disposed within at least at least one portion of an interior of the main body 110, the primary sanitization unit 120 including a sanitization body 121 to automatically move from a second end of the main body 110 to the first end of the main body 110 in response to the main body 110 receiving the at least one shopping cart 10, and at least one illumination unit disposed on at least at least one portion of the sanitization body 120 to automatically illuminate UV light on the at least one shopping cart 10 in response to the main body 110 receiving the at least one shopping cart 10, such that the at least one illumination unit eliminates a pathogen.

The main body 110 may include a barrier 112 disposed on at least at least one portion of the first end of the main body 110, and an inclined surface 114 disposed within at least at least one portion of the first end of the main body 110 to facilitate extraction of the at least one shopping cart 10 from the main body 110.

The main body 110 may receive the at least one shopping cart 10 in response to the barrier 112 being sufficiently closed.

The at least one illumination unit may illuminate in response to the barrier 112 being sufficiently closed.

The at least one illumination unit may comprise at least at least one form of a UV light.

The main body 110 may allow visible light with respect to humans to move therethrough and prevent the UV light from moving therethrough.

The main body 110 may prevent the UV light from moving therethrough using polycarbonate or other transparent or translucent materials, either by merits of the other transparent or translucent materials or an addition of specialty coatings.

The main body 110 may allow visible light with respect to humans to move therethrough and reflect the UV light toward the interior of the main body 110.

The main body 110 may reflect or absorb the UV light using barium sulphate or any other reflective material.

The shopping cart sanitization device 100 may further include a sensor 160 disposed on at least at least one portion of the main body 110 to detect receipt of the at least one shopping cart 10 within the main body 110.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A shopping cart sanitization device, comprising:
a main body to receive at a first end at least one shopping cart therein;
a sensor disposed on at least at least one portion of the main body to detect receipt of the at least one shopping cart within the main body;
a rail assembly, comprising:
  a plurality of rails disposed on at least one portion of a base of the main body to connect to the at least one shopping cart; and
a primary sanitization unit disposed within at least one portion of an interior of the main body, the primary sanitization unit comprising:
  a sanitization body connected to a top surface of the plurality of rails to automatically move on the plurality of rails from a second end of the main body to the first end of the main body in response to the main body receiving the at least one shopping cart, and
  at least one illumination unit disposed on at least one portion of the sanitization body to automatically illuminate UV light on the at least one shopping cart in response to the sensor activating the at least one illumination unit after detecting the main body receives the at least one shopping cart, such that the at least one illumination unit eliminates a pathogen.

2. The shopping cart sanitization device of claim 1, wherein the main body comprises:
a barrier disposed on at least one portion of the main body; and
an inclined surface disposed within at least at least one portion of the main body to facilitate extraction of the at least one shopping cart from the main body.

3. The shopping cart sanitization device of claim 2, wherein the main body receives the at least one shopping cart in response to the barrier being closed.

4. The shopping cart sanitization device of claim 2, wherein the at least one illumination unit illuminates in response to the barrier being closed.

5. The shopping cart sanitization device of claim 1, wherein the at least one illumination unit comprises at least one form of a UV light.

6. The shopping cart sanitization device of claim 1, wherein the main body allows visible light with respect to humans to move therethrough and prevent the UV light from moving therethrough.

7. The shopping cart sanitization device of claim 6, wherein the main body prevents the UV light from moving therethrough using polycarbonate or other transparent or translucent materials.

8. The shopping cart sanitization device of claim 1, wherein the main body allows visible light with respect to humans to move therethrough and reflect or absorb the UV light toward the interior of the main body.

9. The shopping cart sanitization device of claim 8, wherein the main body reflects or absorbs the UV light using barium sulphate or any other reflective material.

10. A shopping cart sanitization device, comprising:
a main body having a spiral shape, the main body to receive at a first end at least one shopping cart therein, such that a second end of the main body is at a higher elevation that the first end of the main body;
a sensor disposed on at least at least one portion of the main body to detect receipt of the at least one shopping cart within the main body; and
a primary sanitization unit disposed within at least one portion of an interior of the main body, the primary sanitization unit comprising:
  a sanitization body to automatically move from the second end of the main body to the first end of the main body in response to the main body receiving the at least one shopping cart, and
  at least one illumination unit disposed on at least one portion of the sanitization body to automatically illuminate UV light on the at least one shopping cart in response to the sensor activating the at least one illumination unit after detecting the main body receives the at least one shopping cart, such that the at least one illumination unit eliminates a pathogen.

* * * * *